(12) United States Patent
Rostami et al.

(10) Patent No.: US 11,013,267 B2
(45) Date of Patent: May 25, 2021

(54) NON-COMBUSTIBLE TOBACCO VAPING INSERT, AND A CARTRIDGE CONTAINING THE NON-COMBUSTIBLE TOBACCO VAPING INSERT

(71) Applicant: Altria Client Services LLC, Richmond, VA (US)

(72) Inventors: Ali A. Rostami, Glen Allen, VA (US); San LI, Midlothian, VA (US); Yezdi B. Pithawalla, Midlothian, VA (US)

(73) Assignee: Altria Client Services LLC, Richmond, VA (US)

( * ) Notice: Subject to any disclaimer, the term of this patent is extended or adjusted under 35 U.S.C. 154(b) by 732 days.

(21) Appl. No.: 15/712,357

(22) Filed: Sep. 22, 2017

(65) Prior Publication Data

US 2019/0090539 A1 Mar. 28, 2019

(51) Int. Cl.
*A24F 47/00* (2020.01)
*A61M 11/04* (2006.01)
(Continued)

(52) U.S. Cl.
CPC .............. *A24F 47/008* (2013.01); *A24D 1/04* (2013.01); *A61M 11/042* (2014.02); *A61M 15/06* (2013.01); *H02J 7/0045* (2013.01); *A24D 3/00* (2013.01); *A61M 11/003* (2014.02); *A61M 15/0003* (2014.02); *A61M 15/0021* (2014.02);
(Continued)

(58) Field of Classification Search
None
See application file for complete search history.

(56) References Cited

U.S. PATENT DOCUMENTS

| 3,583,406 A | 6/1971 | Soyars et al. |
| 4,474,192 A | 10/1984 | MacLean et al. |

(Continued)

FOREIGN PATENT DOCUMENTS

| EP | 0501181 A1 | 9/1992 |
| EP | 2394520 A1 | 12/2011 |

(Continued)

OTHER PUBLICATIONS

Definition of "diameter" (Merriam-Webster online dictionary), [online], retrieved from the Internet, [retrieved Sep. 24, 2018], <URL:https://www.merriam-webster.com/dictionary/diameter>. (Year: 2018).*

(Continued)

*Primary Examiner* — Dennis R Cordray
(74) *Attorney, Agent, or Firm* — Harness, Dickey & Pierce, P.L.C.

(57) ABSTRACT

The non-combustible tobacco vaping insert includes a filter having a first diameter, and a non-combustible tobacco element with a first end contacting the filter. At least one first portion of the tobacco element has a second diameter that is smaller than the first diameter of the filter. The cartridge includes a heater configured to vaporize a pre-vapor formulation that is communicated to the heater by a wick. The insert is positioned in at least a portion of an air passage within cartridge, where the insert is configured to allow vapor that is generated by the heater to pass through the insert prior to being discharged from the cartridge.

17 Claims, 5 Drawing Sheets

(51) Int. Cl.
    *A24D 1/04*         (2006.01)
    *A61M 15/06*      (2006.01)
    *H02J 7/00*         (2006.01)
    A61M 15/00      (2006.01)
    A24D 3/00       (2020.01)
    A61M 16/00      (2006.01)
    H02J 7/34        (2006.01)
    A61M 11/00      (2006.01)

(52) U.S. Cl.
    CPC ............ *A61M 2016/0021* (2013.01); *A61M 2205/8206* (2013.01); *H02J 7/342* (2020.01)

(56) References Cited

U.S. PATENT DOCUMENTS

| | | | |
|---|---|---|---|
| 4,498,487 A | 2/1985 | Frattolillo | |
| 4,510,950 A | 4/1985 | Keritsis et al. | |
| 5,082,008 A | 1/1992 | Johnson | |
| 5,240,016 A | 8/1993 | Nichols et al. | |
| 5,388,596 A | 2/1995 | Schneider et al. | |
| 5,396,911 A | 3/1995 | Casey, III et al. | |
| 5,490,876 A * | 2/1996 | Warmerdam | A24C 5/24 106/209.1 |
| 5,692,526 A | 12/1997 | Adams et al. | |
| 5,954,060 A | 9/1999 | Cardarelli | |
| 5,954,061 A | 9/1999 | Cardarelli | |
| 8,235,056 B2 | 8/2012 | Zhuang et al. | |
| 2008/0092912 A1 | 4/2008 | Robinson et al. | |
| 2011/0180081 A1 | 7/2011 | Fiebelkom | |
| 2011/0290269 A1* | 12/2011 | Shimizu | A61M 15/0023 131/330 |
| 2013/0014772 A1 | 1/2013 | Liu | |
| 2014/0261492 A1 | 9/2014 | Kane et al. | |
| 2014/0305448 A1 | 10/2014 | Zuber et al. | |
| 2014/0305449 A1 | 10/2014 | Plojoux et al. | |
| 2014/0356607 A1 | 12/2014 | Woodcock | |
| 2015/0013697 A1 | 1/2015 | Mironov | |
| 2015/0040922 A1 | 2/2015 | Dube et al. | |
| 2015/0040925 A1 | 2/2015 | Saleem et al. | |
| 2015/0257439 A1 | 9/2015 | Tritz et al. | |
| 2017/0238596 A1* | 8/2017 | Matsumoto | A61K 9/007 |
| 2017/0238605 A1* | 8/2017 | Matsumoto | A61M 11/065 |

FOREIGN PATENT DOCUMENTS

| | | |
|---|---|---|
| GB | 2012554 A | 8/1979 |
| WO | WO-2012/016795 A1 | 2/2012 |
| WO | WO-2013/000967 A1 | 1/2013 |
| WO | WO-2013/060607 A1 | 5/2013 |
| WO | WO-2013/098410 A2 | 7/2013 |
| WO | WO-2017/149152 A1 | 9/2017 |

OTHER PUBLICATIONS

Written Opinion of the International Preliminary Examining Authority dated Aug. 22, 2019 in corresponding International Application No. PCT/EP2018/075540.
Written Opinion of the International Preliminary Examining Authority dated Dec. 12, 2019 in corresponding International Application No. PCT/EP2018/075540.
V2 Pro Manual, Retrieved Apr. 18, 2016 from: https://www.v2.com/templates/v2v3/Download/V2PRO-S7-UserManual-0815.pdf.
Ismoke Oven, Downloaded Apr. 18, 2016 from: http://www.ismoke.com/themes/defaultclean/content/Usermanual-oven.pdf.
Bat Ifuse, Nov. 22, 2015, http://www.ft.com/intl/cms/s/0/07b0c5fa-8e21-11e5-a549-b89a1dfede9b.html#axzz46C3HIeKc.
International Preliminary Report on Patentability dated Mar. 17, 2020 in corresponding International Application No. PCT/EP2018/075540.
International Search Report and Written Opinion dated Jan. 2, 2019 in corresponding European Application No. PCT/EP2018/075540.

* cited by examiner

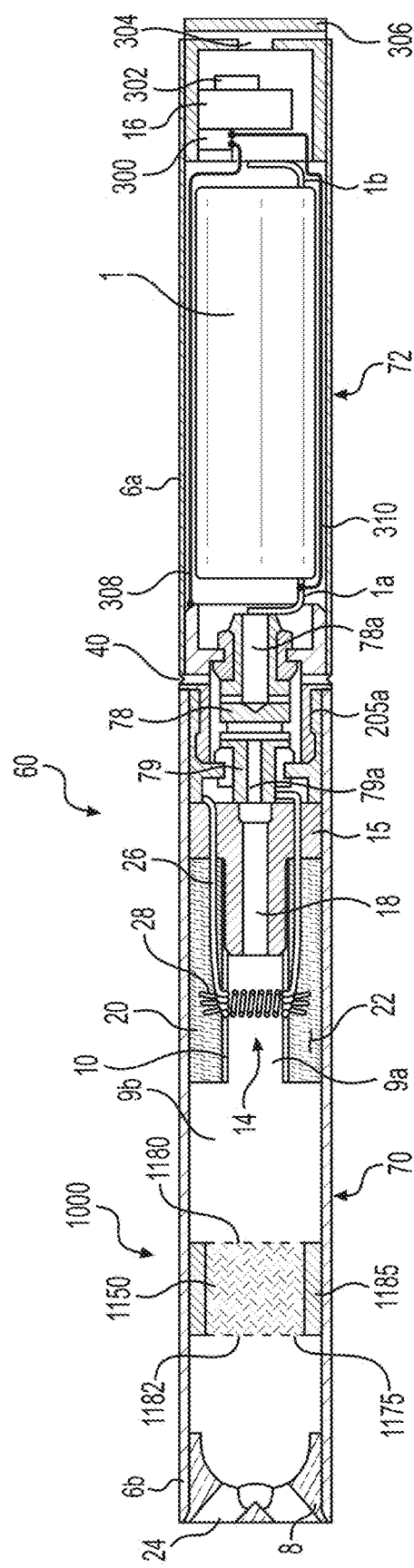
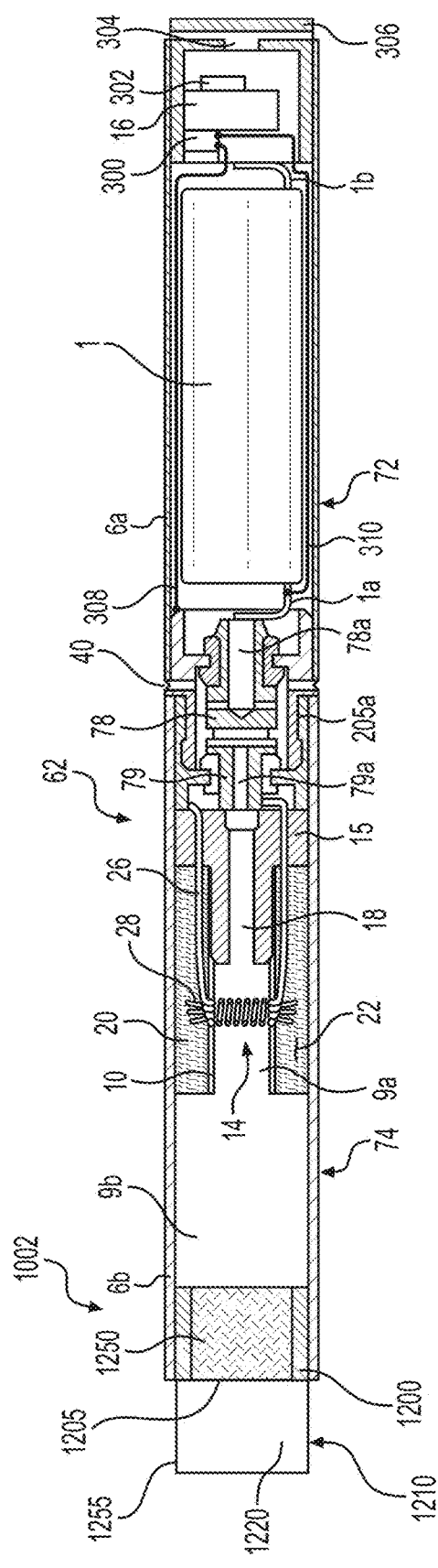
FIG. 1
FIG. 2

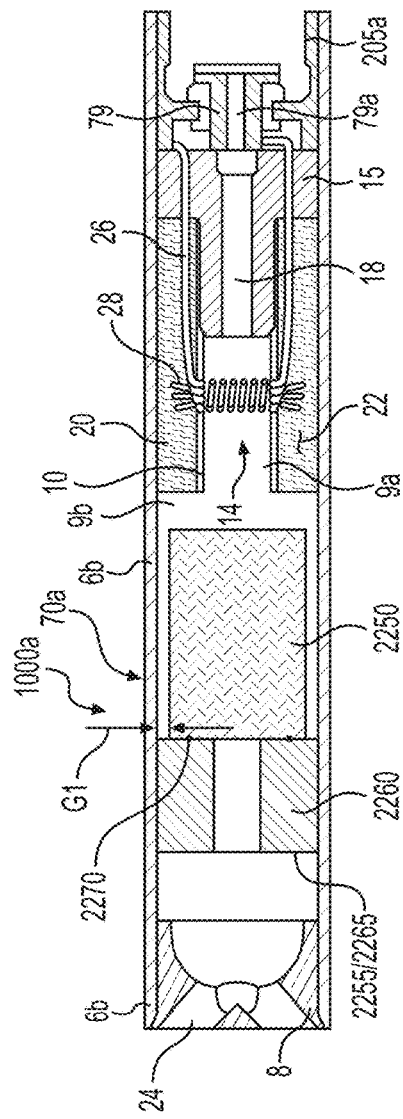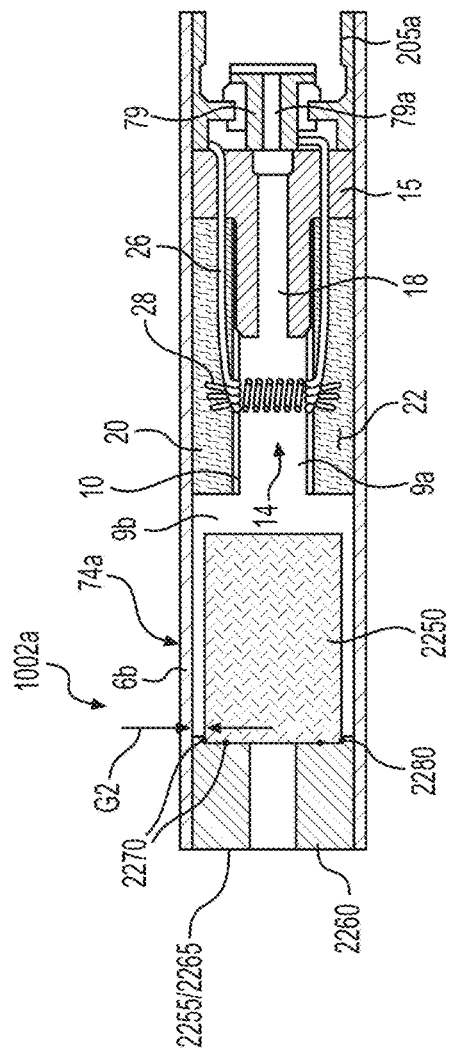

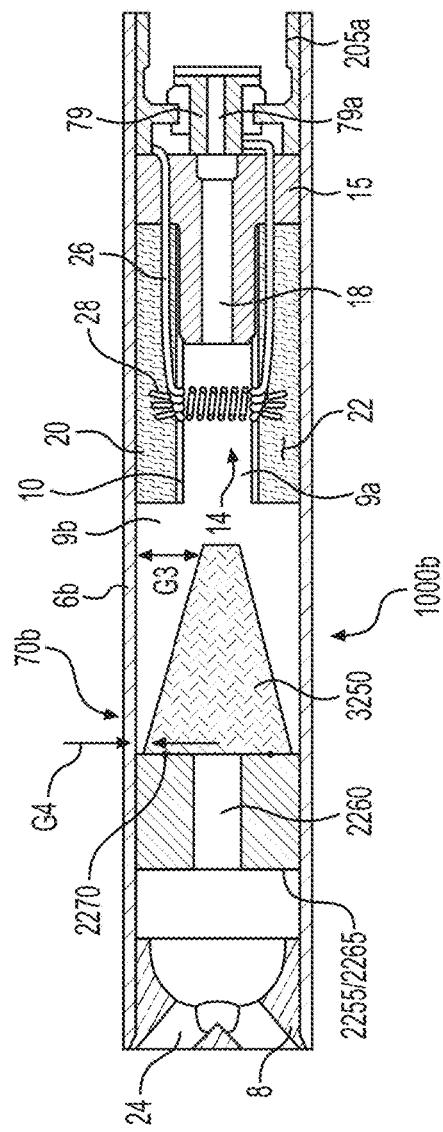
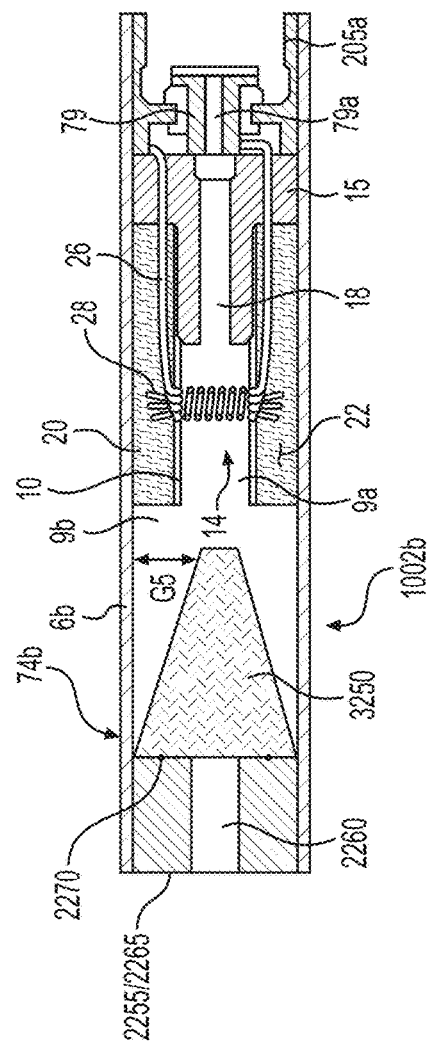

… (1 / 24)

NON-COMBUSTIBLE TOBACCO VAPING INSERT, AND A CARTRIDGE CONTAINING THE NON-COMBUSTIBLE TOBACCO VAPING INSERT

BACKGROUND

Field

Example embodiments relate generally to a non-combustible tobacco vaping insert, and a cartridge containing the non-combustible tobacco vaping insert.

Related Art

Combination tobacco and vapor systems may include a vapor generating portion and a tobacco column. The tobacco column may be used to add additional tobacco flavors to vapor exiting the vapor generating portion.

SUMMARY

At least one example embodiment is directed toward a non-combustible tobacco vaping insert.

In one embodiment, the non-combustible tobacco vaping insert includes, a filter having a first diameter; and a non-combustible tobacco element with a first end contacting the filter, wherein at least one first portion of the tobacco element has a second diameter that is smaller than the first diameter of the filter.

In one embodiment, the tobacco element has a uniform diameter along a longitudinal length of the tobacco element, the uniform diameter being the second diameter.

In one embodiment, the tobacco element has a varying diameter, and the first end of the tobacco element has a third diameter.

In one embodiment, the third diameter is a largest diameter of the tobacco element, along a longitudinal length of the tobacco element.

In one embodiment, the third diameter of the tobacco element is smaller than the first diameter of the filter.

In one embodiment, the third diameter of the tobacco element is equal to the first diameter of the filter.

In one embodiment, the tobacco element is a conical shape.

In one embodiment, the tobacco element is a cylindrical shape.

In one embodiment, the tobacco element is in the shape of a thin sheet.

In one embodiment, the first end of the tobacco element is connected to the filter via an adhesive, the adhesive being at least one of a starch-based adhesive and a dextrin-based adhesive.

In one embodiment, the first end of the tobacco element is embedded into a surface of the filter.

In one embodiment, the tobacco element includes at least one of tobacco leaf, compressed tobacco, tobacco strands, rolled tobacco, reconstituted tobacco, filler, tobacco beads, compressed tobacco rod, shaped tobacco and tobacco powder.

In one embodiment, the tobacco element further includes flavoring elements, the flavoring elements being one of a tobacco-flavoring and another flavoring that is not tobacco-flavoring.

In one embodiment, the filter is one of a cellulose acetate (CA) filter and a hollow-acetate-tube (HAT) filter.

At least another example embodiment relates to a cartridge including a non-combustible tobacco vaping insert.

In one embodiment, the non-combustible tobacco vaping insert includes, a housing; a reservoir within the housing, the reservoir configured to contain a pre-vapor formulation; a first tube extending longitudinally within the housing, wherein at least one of the first tube and the housing at least partially defines an air passage; a wick in communication with at least one first portion of the air passage, distal ends of the wick being in communication with the reservoir; a heater configured to vaporize the pre-vapor formulation that is communicated to the heater by the wick; and a non-combustible tobacco vaping insert being positioned in at least one second portion of the air passage, the non-combustible tobacco vaping insert being configured to allow vapor that is generated by the heater to pass through the non-combustible tobacco vaping insert prior to being discharged from the cartridge, the non-combustible tobacco vaping insert including, a filter having a first diameter, and a non-combustible tobacco element with a first end contacting the filter, at least one first portion of the tobacco element having a second diameter that is smaller than the first diameter of the filter.

In one embodiment, the first diameter of the filter of the non-combustible tobacco vaping insert fills a diameter of the at least one second portion of the air passage, and an annular gap exists between at least a portion of an outer surface of the tobacco element of the non-combustible tobacco vaping insert and the at least one second portion of the air passage, along at least a portion of a longitudinal length of the tobacco element.

In one embodiment, the annular gap exists along a longitudinal length of the tobacco element.

In one embodiment, the annular gap varies in thickness along a longitudinal length of the tobacco element.

In one embodiment, the annular gap has a thickness that is about 5% to 40% of the linear length of the first diameter of the filter.

In one embodiment, the heater is configured to be in thermal communication with the tobacco element in order to heat at least a portion of the tobacco element.

At least another example embodiment relates to a non-combustible tobacco vaping insert.

In one embodiment, the non-combustible tobacco vaping insert includes a filter having a first cross-sectional width; and a non-combustible tobacco element with a first end contacting the filter, wherein at least one first portion of the tobacco element has a second cross-sectional width that is smaller than the first cross-sectional width of the filter.

BRIEF DESCRIPTION OF THE DRAWINGS

The above and other features and advantages of example embodiments will become more apparent by describing in detail, example embodiments with reference to the attached drawings. The accompanying drawings are intended to depict example embodiments and should not be interpreted to limit the intended scope of the claims. The accompanying drawings are not to be considered as drawn to scale unless explicitly noted.

FIG. 1 illustrates an electronic vaping (e-vaping) device that includes a non-combustible tobacco vaping insert;

FIG. 2 illustrates another e-vaping device that includes a non-combustible tobacco vaping insert;

FIG. 3A illustrates an e-vaping cartridge with a non-combustible tobacco vaping insert including a tobacco element, in accordance with an example embodiment;

FIG. 3B illustrates another e-vaping cartridge with a non-combustible tobacco vaping insert including a tobacco element, in accordance with an example embodiment;

FIG. 4A illustrates an e-vaping cartridge with a non-combustible tobacco vaping insert including a conical-shaped tobacco element, in accordance with an example embodiment;

FIG. 4B illustrates another e-vaping cartridge with a non-combustible tobacco vaping insert including a conical-shaped tobacco element, in accordance with an example embodiment;

DETAILED DESCRIPTION

Figure 5A:
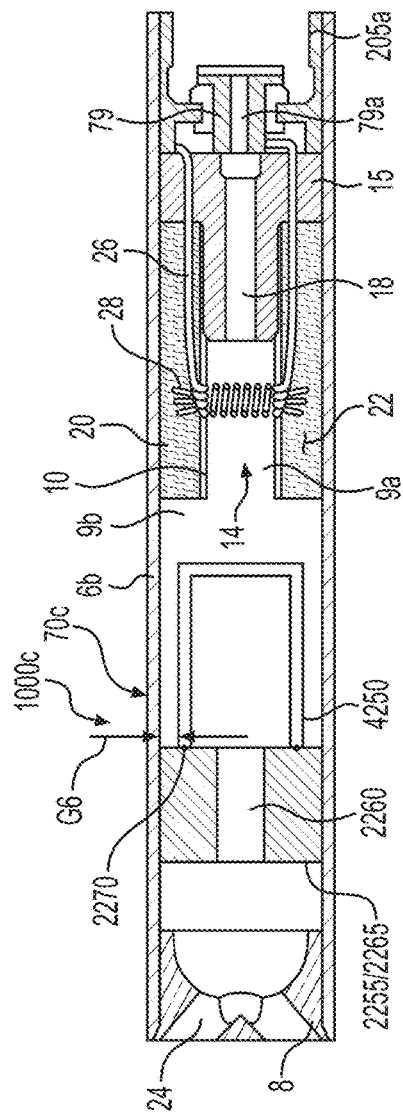
FIG. 5A illustrates an e-vaping cartridge with a non-combustible tobacco vaping insert including a tobacco element in the shape of a sheet, in accordance with an example embodiment.

Some detailed example embodiments are disclosed herein. However, specific structural and functional details disclosed herein are merely representative for purposes of describing example embodiments. Example embodiments may, however, be embodied in many alternate forms and should not be construed as limited to only the embodiments set forth herein.

Accordingly, while example embodiments are capable of various modifications and alternative forms, embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

General Structure of an E-Vaping Device with a Non-Combustible Tobacco Vaping Insert In some systems, including tobacco vapor systems, a fraction of the tobacco in the tobacco column is available to be heated by incoming vapor from the vapor generating portion of the system, while remaining portions of the tobacco in the tobacco column may remain unaffected by heating. This may cause a reduced amount of flavor to be added to the vapor exiting the vapor generating portion. Additionally, a temperature of the vapor in a tobacco vapor system may reach an ambient temperature, or a near-ambient temperature, at a discharge of the tobacco column portion of the tobacco vapor system, which is generally undesirable. Furthermore, in tobacco vapor systems, a vapor flow path through the tobacco column may cause significant vapor loss due to undesirable filtration of the vapor as it passes through the tobacco column. Meanwhile, the tobacco column may create a relatively high pressure drop for the vapor flowing through the tobacco column, which may in turn increase an overall effective resistance to draw (RTD) of an e-vaping device that may include a tobacco vapor system.

FIG. 1 illustrates an electronic vaping (e-vaping) device 60 that includes a non-combustible tobacco vaping insert 1000. Specifically, the device 60 may include a cartridge section 70 that includes the insert 1000. The insert 1000 may include a cylindrical housing 1185 that may be pressure-fitted into an outer air passage 9*a*, or a second outer air passage 9*b* (notice that FIG. 1 shows the insert 1000 only in the second outer air passage 9*b*), that may be near a mouth-end insert 8 of the device 60. Alternatively to pressure-fitting the housing 1185 within the outer air passages 9*a* or 9*b*, the housing 1185 may instead be held within the housing 6*b* of section 70, or alternatively held within the inner tube 10 of section 70, via an adhesive, set screws, a snap-fit connecting structure, or any other structure necessary to hold the housing 1185 of the insert 1000 in place within section 70. Furthermore, the insert 1000 may either be permanently affixed within section 70, or alternatively insert 1000 may be temporarily held within section 70, such that insert 1000 may be removed and then replaced prior to the useful end-life of section 70. The housing 1185 may be a cylindrical housing made of aluminum, for example. The cylindrical housing 1185 may have an outer diameter that fits with the diameter of the second outer air passage 9*b* (or similarly, the diameter of the outer passage 9*a*, in the event that the housing 1185 is affixed within inner tube 10).

The insert 1000 may include a tobacco element 1150. The term "tobacco element" may refer to any tobacco plant material including tobacco leaf, tobacco plug (compressed form of tobacco), tobacco strands, rolled tobacco, reconstituted tobacco, filler, tobacco beads, compressed tobacco rod, shaped tobacco, and/or powder tobacco, for example. The tobacco element 1150 may be wrapped in natural tobacco, reconstituted sheet tobacco or aluminum, for example. In an alternative embodiment, flavor elements may be substituted for "tobacco elements" (as described herein), where "tobacco elements" may be one type of a "flavor element." The term "flavor element" may also include non-combustible flavor beads, flavor elements, or flavored-tobacco elements, where the flavoring may be something other than a tobacco flavoring, or the flavoring may include another flavoring in addition to a tobacco flavoring. While only one tobacco element 1150 is illustrated in FIG. 1, it should be understood that a plurality of tobacco elements 1150 may be used. Fibrous segments (e.g., cellulose acetate, other synthetic fibers, or natural fibers) may be placed between the plurality of tobacco plugs. The tobacco element 1150 may be a "non-combustible" element that may be capable of introducing tobacco flavoring to heated vapor that may pass through the element 1150 (as described below in more detail), without the element 1150 being burned or otherwise combusted.

Mesh screens 1175 and 1180 may fit on the ends of the housing 1185 to enclose the tobacco element 1150 within the housing 1185. The mesh screens 1175 and 1180 may include openings 1182 that may allow vapor to pass from one end of the housing 1185 through the tobacco element 1150 and out of the end of the housing 1185 that is closest to the mouth-end insert 8.

As shown in FIG. 1, the insert 1000 may be an element of a section 70 of the e-vaping device 60, where the section 70 may be a cartridge. The section 70 may be a disposable section, or optionally the section 70 may instead be a non-disposable (rechargeable) section. The section 70 may include a heater 14 surrounding a wick 28, where distal ends of the wick 28 may protrude into a reservoir 20 that make contain a pre-vapor formulation 22. The reservoir 20 may be at least partially defined by inner tube 10 and housing 6*b* of section 70. The heater 14 may be positioned within inner tube 10, where the wick 28 may draw the pre-vapor formulation 22 from the reservoir, via a capillary action, in order for the heater 14 to heat and vaporize the pre-vapor formulation 22.

In an embodiment, the wick 28 may be constructed of a fibrous and flexible material. The wick 28 may include at least one filament having a capacity to draw the pre-vapor formulation 22. For example, the wick 28 may include a bundle of filaments which may include glass (or ceramic) filaments. In another embodiment, a bundle may include a group of windings of glass filaments, for example, three of such windings, all which arrangements are capable of drawing pre-vapor formulation 22 via capillary action via interstitial spacing between the filaments.

In an embodiment, the heater 14 may be in the form of a wire coil, a planar body, a ceramic body, a single wire, a cage of resistive wire, or any other suitable form that may be configured to vaporize a pre-vapor formulation. The heater 14 may at least partially surround the wick 28. The heater 14 may extend fully or partially along a length of the wick 28, where the heater 14 may extend fully or partially around the circumference of the wick 28. In some example embodiments, the heater 14 may or may not be in contact with the wick 28.

In at least one example embodiment, the heater 14 may be formed of any suitable electrically resistive materials. Examples of suitable electrically resistive materials may include, but not limited to, copper, titanium, zirconium, tantalum and metals from the platinum group. Examples of suitable metal alloys include, but not limited to, stainless steel, nickel, cobalt, chromium, aluminum-titanium-zirconium, hafnium, niobium, molybdenum, tantalum, tungsten, tin, gallium, manganese and iron-containing alloys, and super-alloys based on nickel, iron, cobalt, stainless steel. For example, the heater 14 may be formed of nickel aluminide, a material with a layer of alumina on the surface, iron aluminide and other composite materials, the electrically resistive material may optionally be embedded in, encapsulated or coated with an insulating material or vice-versa, depending on the kinetics of energy transfer and the external physicochemical properties required. The heater 14 may include at least one material selected from the group consisting of stainless steel, copper, copper alloys, nickel-chromium alloys, super alloys and combinations thereof. In an example embodiment, the heater 14 may be formed of nickel-chromium alloys or iron-chromium alloys. In another example embodiment, the heater 14 may be a ceramic heater having an electrically resistive layer on an outside surface thereof.

In another embodiment, the heater 14 may be constructed of an iron-aluminide (e.g., FeAl or $Fe_3Al$). Use of iron-aluminides can be advantageous in that they may exhibit high resistivity. FeAl may exhibit a resistivity of approximately 180 micro-ohms, whereas stainless steel may exhibit approximately 50 to 91 micro-ohms. The higher resistivity lowers current may draw or load on a power source 1 of section 72 of the device 60.

The mouth-end insert 8 of section 70 may either be permanently affixed on an end of the section 70, or alternatively mouth-end insert 8 may be removable. In the event that mouth-end insert 8 is removable, the insert 1000 may optionally also be removable and/or replaceable. Another end of section 70 may be at least partially sealed by seal 15. Seal 15 may define a central air passage 18, where central passage 18 may be in fluid communication with the outer air passage 9a (where outer air passage 9a may be at least partially defined by inner tube 10), so that air may flow through central air passage 18, and then through outer air passage 9a, when the section 70 is in operational use.

An anode terminal 79 may be affixed to an end of section 70, near the seal 15. The anode terminal 79 may at least partially held in place by connector 205. Connector 205 may be a female connector. Alternatively, connector 205 of section 70 may instead be a male connector. Electrical leads 26a/b may be attached to both ends of heater 14, in order to provide electrical power to the heater 14. Specifically, electrical lead 26a may be electrically connected to connector 205 (where connector 205 may be electrically conductive), and electrical lead 26 be may be electrically connected to anode terminal 79.

A position of the heater 14 is not limited to the position shown in FIG. 1, nor is the precise position of the insert 1000 limited to the position shown in FIG. 1. For example, the heater 14 may be positioned at an end of the outer air passage 9a, such that the heater 14 may be closer to the tobacco element 1250 and/or in contact, or near contact, with the tobacco element 1250. In an example embodiment, the heater 14 may protrude out of the outer air passage 9a, and into the second outer air passage 9b. Meanwhile, the insert 1000 may be set closer to the mouth-end insert 8, or closer to the outer air passage 9a. Furthermore, the insert 1000 may be positioned in the narrower outer air passage 9a, either in lieu of the insert 1000 being positioned in the second outer air passage 9b, or in addition to an insert 1000 also being positioned in the second air passage 9b. That is to say, there may be more than one insert 1000 within the cartridge 70.

The heater 14 may be positioned a distance apart from the tobacco element 1250, or alternatively the heater 14 may contact the tobacco element 1250 such that the heater 14 may heat the tobacco element 1250 to a desired temperature during an application of a negative pressure (as described in more detail below). The heater 14 may warm the tobacco element 1150, but does not burn the tobacco element 1150. Thus, the warming of the tobacco element 1150 may be referred to as "non-combustible." Because the section 70 may include the tobacco element 1150 and the heater 14, the section 70 may be referred to as a "non-combustible smoking element."

In an embodiment, the pre-vapor formulation 22 may be a material or combination of materials that may be transformed into a vapor. For example, the pre-vapor formulation 22 may be a liquid, solid and/or gel formulation including, but not limited to, water, beads, solvents, active ingredients, ethanol, plant extracts, natural or artificial flavors, and/or vapor formers such as glycerin and propylene glycol.

The pre-vapor formulation 22 may include volatile tobacco flavor compounds which may be released upon heating. The pre-vapor formulation 22 may also include tobacco elements dispersed throughout the formulation 22. When tobacco elements are dispersed in the pre-vapor formulation 22, the physical integrity of the tobacco element may be preserved. For example, the tobacco element may be 2-30% by weight within the pre-vapor formulation 22. Alternatively, the pre-vapor formulation 22 may be flavored with other flavors besides a tobacco flavor, or in addition to a tobacco flavor.

The reservoir 20 may be defined in an annulus space between the inner tube 10 and the housing 6b of the cartridge 70. The reservoir 20 may contain the pre-vapor formulation 22, and the reservoir 20 may optionally include a storage medium (not shown) configured to store the pre-vapor formulation 22 therein. The storage medium may include a winding of cotton gauze, a fibrous material, polyethylene, polyester, rayon and/or combinations thereof that may be wound around the inner tube 10.

Section 70 may be connectable to section 72 of the e-vaping device 60, where section 72 may be a power section that may include a power supply 1. The power supply 1 may be a battery, such as a lithium ion battery. The battery may be a Lithium-ion battery or one of its variants, for example a Lithium-ion polymer battery. Alternatively, the battery may be a Nickel-metal hydride battery, a Nickel cadmium battery, a Lithium-manganese battery, a Lithium-cobalt battery or a fuel cell. In that case, power section 72 may be usable until the energy in the power supply 1 is depleted. Alternatively, the power supply 1 may be rechargeable and reusable, and may include circuitry allowing the battery to be chargeable by an external charging device. In that case, the circuitry, when charged, may provide power for a desired (or alternatively, a determined) number of draws, after which the circuitry must be re-connected to an external charging device.

The power source 1 may have electrical connections 1a/b emanating from the power source 1. For instance, the power source 1 may have an anode connection 1a and a cathode connection 1b that may help create an electrical circuit to power the operations of the device 60. For instance, the power source 1 may be electrically connected to a sensor 16 and a control circuit 300 that may control an operation of the device 60. The control circuit 300 may be disposed on a rigid printed circuit board 302. The circuit board 302 may be connected to the first electrical connection 1a of the power supply 1 via electrical lead 308, and the circuit board 302 may be connected to the second electrical connection 1b via electrical lead 310. The power source 1 may also send an electrical current to the heater 14 of the cartridge 70 (as explained below in more detail).

The cartridge section 70 may be connectable to the power section 72, via mating threads 205a/b. Alternatives to threads 205a/b, other structure may be used to connect the sections 70/72 to each other. For instance, friction fitting, snap fitting, adhesive, a removable and/or insertable pin, or other suitable structure may be used to join the sections 70/72 to each other. Optionally, the power section 72 may be permanently connected to the cartridge 70, such that the power section 72 may be an integral section of the cartridge 70.

Upon joining the sections 70/72 of the e-vaping device 60, air flow paths may exist in order to communicate an air flow between the sections 70/72. Specifically, an anode electrical post 78 of the power section 72 may define an air passage 78a through the post 78. The air passage 78a of post 78 may be in fluid communication with an air passage 79a that may be defined by anode terminal 79 of section 70 of the e-vaping device 60, where the air passages 79a/78a may allow the internal cavity of section 72 to be in fluid communication with the central air passage 18 of section 70. One or more air inlets 40 may be defined by connector 206 of section 72, where the air inlets 40 may also be in fluid communication with air passages 79a/78a. In an embodiment, the air inlets 40 may be positioned at several locations around a periphery of section 72.

In an assembled state, the e-vaping device 60 may form an electrical circuit that powers the operations of the device 60. The circuit may include the power source 1, the sensor 16, the control circuit 300, electrical leads 308/310, connectors 205/206 (where these connectors 205/206 may be made from an electrically conductive metal), the posts 78/78, the electrical leads 26a/b, and the heater 14.

The E-Vaping Device in Operational Use

Based on a structural understanding of the e-vaping device 60, as described above, an operation of the assembled device 60 is explained herein. Airflow through the device 60 may be caused by air being drawn into the cartridge 70 primarily from the air inlets 40, where the air may flow through the air passage 79a of the anode terminal 79, through the central air passage 18 and into the outer air passage 9a. In outer air passage 9a, the airflow may become entrained (eluted) by vapor that may be produced by the heater 14 heating the pre-vapor formulation 22 absorbed via the wick 28, prior to the airflow with the entrained vapor being discharged through the second outer air passage 9b. In the second outer air passage 9b, the heated vapor may pass through the tobacco element 1150 of the insert 1000 in order to allow the vapor to become entrained by added tobacco flavoring from the tobacco element 1150, prior to the flavored vapor being discharged from the device 60 via the diverging outlets 24 of the mouth-end insert 8.

Because the air passage 78a of post 78 may be in fluid communication with the air passage 79a of post 79, the sensor 16 may then be capable of detecting vaping conditions (discussed below), so that the control circuit 300 may provide an electrical current from the power supply 1 to the heater 14 in order to heat and vaporize the pre-vapor formulation 22 that may be drawn to the heater 14 via the wick 28. In an embodiment, when activated, the heater 14 may heat a portion of the wick 28 for less than about 10 seconds.

The airflow through the device 60 may be used to activate the device 60. Specifically, the sensor 16 may be configured to generate an output indicative of a magnitude and direction of the airflow, where the control circuit 300 may receive the sensor 16 output and determine if the following vaping conditions exist: (1) a direction of the airflow indicates a draw on the mouth-end insert 8 (versus blowing air through the insert 8), and (2) a magnitude of the airflow exceeds a threshold value. If these internal vaping conditions of the device 60 are met, the control circuit 300 may electrically connect the power supply 1 to the heater 14, thereby activating the heater 14. Namely, the control circuit 300 may electrically connect the electrical lead 310 and electrical connection 1b (by activating a heater power control transistor forming part of the control circuit 300) so that the heater 14 may become electrically connected to the power supply 1. In an alternate embodiment, the sensor 16 may generate an output indicative of a pressure drop whereupon the control circuit 300 may activate the heater 14, in response thereto.

In an embodiment, the control circuit 300 may include a light 304, which the control circuit 300 may activate to glow when the heater 14 is activated and/or the power supply 1 is recharging. The light 304 may include one or more light-emitting diodes (LEDs). The LEDs may include one or more colors (e.g., white, yellow, red, green, blue, etc.). Moreover, the light 304 may be arranged to be visible to an adult tobacco consumer during vaping, where the light 304 may be positioned near the endcap 306 of the power section 72 of the e-vaping device 60. The light 304 may also be utilized for e-vaping system diagnostics. The light 304 may be configured such that an adult tobacco consumer may activate and/or deactivate the heater activation light 304 for privacy.

In an embodiment, the control circuit 300 may include a time-period limiter. In another embodiment, the control circuit 300 may include a manually operable switch for an adult tobacco consumer to initiate heating. The time-period of the electric current supply to the heater 14 may be set or pre-set depending on an amount of pre-vapor formulation 22 desired to be vaporized.

Another Structure of an E-Vaping Device with a Non-Combustible Tobacco Vaping Insert FIG. 2 illustrates another e-vaping device 62 that includes a non-combustible tobacco vaping insert 1002. Elements of the device 62 of FIG. 2 that are common with elements of the device of FIG. 1 are not discussed herein, for brevity sake. As shown in FIG. 2, the device 62 may include an insert 1002 that may be included on an end of the device 62. In particular, the insert 1002 may be fitted on an end of the cartridge section 74 of the device 62, where a filter 1220 of the insert 1002 may take the place of a typical mouth-end insert (such as the mouth-end insert 8, shown in FIG. 1). In this configuration, the insert 1002 may, optionally, include a replaceable tobacco insert 1210 within the insert 1002, where the tobacco insert 1210 may be removed and replaced prior to the useful and-life of the cartridge 74, following a depletion of the tobacco element 1250 within the tobacco insert 1210. The tobacco insert 1210 may include a tobacco element 1250 and a filter 1220. The insert 1002 may include a housing 1200 that may define a receiving area 1205 that may hold the replaceable tobacco insert 1210.

The tobacco insert 1210 may, optionally, be a cigarette or cigar, or a portion of a cigarette or a cigar. As an example, the tobacco insert may be a filtered cigarette, a non-filtered cigarette, a cigarillo, a filter tipped cigar filter, a tipped cigar or an untipped cigar/cigarillo, for example. However, example embodiments are not limited thereto. In an example embodiment, if the tobacco insert 1210 is an untipped cigar/cigarillo, the tobacco insert 1210 may not include a filter.

Tipping paper 1255 may overlap the filter 1220 and/or the tobacco element 1250. The tipping paper 1255 may cover surface areas of the tobacco insert 1210 that may extend along an inner surface of housing 6b of cartridge 74. Thus, the tipping paper 1255 may provide stiffness to the tobacco insert 1210, permitting easier insertion of the tobacco insert 1210 within the receiving area 1205. An aluminum foil may also be used to contain the tobacco element 1250, and this aluminum foil may either be included in lieu of the tipping paper 1255, or in addition to the tipping paper 1255. In an embodiment, the filter 1220 may be a cellulose acetate (CA) filter.

General Methodology

There are several factors that affect an overall performance of an e-vaping device with an insert. Some of these factors include, but are not limited to: 1) vapor loss due to filtration of the vapor traveling through a tobacco column, 2) effective heating of the tobacco column of the insert to release flavor, 3) excessive undesired cooling of the vapor due to an incidental heat exchange between the vapor and the tobacco and/or the filter of the insert which may cause condensation of flavors, and 4) a pressure drop of the vapor traveling through the insert that may create an undesired effective resistance-to-draw (RTD) for the e-vaping device.

In order to accommodate for some of these factors in an overall performance of the e-vaping device, example embodiments include a configuration of a tobacco column for an insert that may provide an airspace between a housing of an e-vaping device and the tobacco column. The tobacco column configuration may allow heated vapor to travel fully-through the column with less overall cooling, such that relatively warmer vapor may permeate fully through the tobacco column and exit the e-vaping device at a relatively higher temperature. The column configuration may provide a relatively lower effective pressure drop for vapor traveling through the tobacco column, thereby reducing an overall effective resistance to draw (RTD) for the e-vaping device.

Example embodiments making use of a configuration of a tobacco column for inserts, with an improved shape and geometry of the tobacco column, may provide a shorter overall effective vapor-path for the vapor traveling through the tobacco, that may subsequently result in the following advantageous factors: 1) less vapor loss, 2) lower pressure drop of the vapor traveling through the insert, 3) a relatively higher exit temperature (that may be advantageous from a sensory standpoint), 4) less flavor condensation, and 5) a more uniform heating of the tobacco, which may provide a more consistent flavor release over an effective usage-life of the tobacco column.

SPECIFIC EMBODIMENTS

FIG. 3A illustrates an e-vaping cartridge 70a with a tobacco element 2250 in a non-combustible tobacco vaping insert 1000a, in accordance with an example embodiment. This cartridge 70a may be connected to a power section, such as the power section 72 of FIG. 1. Elements of this cartridge 70a which are common to the elements of cartridge 70 of FIG. 1, are not described herein, for brevity sake. As shown in FIG. 3A, the insert 1000a may be located in the second outer air passage 9b. Alternatively, the insert 1000a may instead be located in the outer air passage 9a (or, more than one inserts 1000a may in the cartridge 70, where an insert 1000a may for instance be positioned in both the outer air passage 9a and the second outer passage 9b).

The insert 1000a may include a tobacco element 2250 that does not fully occupy an inner diameter of a passage that the tobacco element 2250 resides in. That is to say, a gap G1 may exist between an outer surface of the tobacco element 2250 and an inner diameter of the housing 6b of the cartridge 1000a, where this gap G1 may exist along a longitudinal length of the tobacco element 2250 (although the gap G1 may not be a consistent depth along the longitudinal length of the tobacco element 2250), in order to provide a circumferential air space able to distribute a more uniform flow of vapor through the tobacco element 2250. In an embodiment, the gap G1 may narrow to a near-zero depth (i.e., a negligible, or nonexistent depth), at the union between the tobacco element 2250 and the filter 2260), where the gap G1 may be larger, or largest, at the end of the tobacco element 2250 that faces the heater 14.

In an embodiment, the tobacco element 2250 may have a major diameter of about 6-10 mm (at the widest portion of the element 2250), where the gap G1 may be about 2-4 mm in thickness, if the insert 1000a resides within the second outer air passage 9b of the cartridge 70a. In an embodiment, the gap G1 thickness may be between about 5% and 40% of the linear length of the major diameter of the tobacco element 2250 (or, about 5% and 40% of the linear length of the major diameter of the filter 2260), either along the entire length of tobacco element 2250, or along the majority of the length of the tobacco element 2250 (where the gap G1 may optionally taper down to a negligible, or non-existent gap at the end of the tobacco element 2250 that is closest to the discharge of the cartridge 70a). The filter 2260 may have a major outer diameter that is about 6-10 mm, with a hole diameter (traversing through a length of the filter 2260) that may be about 2-4 mm.

The gap G1 may allow warm vapor to be exposed to a greater effective surface area of the tobacco element 2250. The gap G1 may also allow the vapor to experience a lower average travel distance through the tobacco element 2250, thereby causing relatively warmer vapor to contact and permeate through a greater volume of the tobacco element 2250 for more effective mixing, where the vapor remains at a relatively higher average temperature throughout the duration of time that the vapor passes through the tobacco element 2250. The gap G1 may lower a pressure drop of the vapor that travels through the tobacco element 2250, which in turn may lower an effective resistance-to-draw (RTD) for the cartridge 70a. Using this tobacco column 2250 configuration, less vapor loss due to filtration of the vapor through the tobacco column 2250 may be experienced, thereby increasing an added tobacco flavoring to the vapor.

The tobacco element 2250 may, optionally, be a cigarette or cigar, or a portion of a cigarette or a cigar. As an example, the tobacco element 2250 may be a filtered cigarette, a non-filtered cigarette, a cigarillo, a filter tipped cigar filter, a tipped cigar or an untipped cigar/cigarillo, for example. However, example embodiments are not limited thereto.

The tobacco element 2250 may be connected to a filter 2260. The filter 2260 may, for instance, be a cellulose acetate (CA) filter, or a hollow-acetate-tube (HAT) filter. The tobacco element 2250 may be connected to the filter 2260 using an adhesive 2270. The adhesive 2270 may be, for instance, a starch and/or a dextrin-based adhesive, or any other well-known adhesive that may be suitable for an e-vaping device. The adhesive 2270 may be applied to one or more spot locations between the tobacco element 2250 and the filter 2260, or alternatively, the adhesive 2270 may effectively cover the union between the tobacco element 2250 and the filter 2260. Due to the existence of gap G1, the width and/or diameter of the filter 2260 may be greater than the width and/or diameter of the tobacco element 2250, such that the filter 2260 may fully fill the air passage that the insert 1000a resides in. In other words, the width and/or diameter of the filter 2260 may fully fill the width and/or diameter of housing 6b within the second outer air passage 9b (or, alternatively, the width and/or diameter of the filter 2260 may fully fill the width and/or diameter of the inner tube 10 within the outer air passage 9a).

Tipping paper 2255 may overlap the filter 2260 and/or the tobacco element 2250. The tipping paper 2255 may, for instance, cover all outer surface of the insert 1000a, or only a portion of the outer surfaces of the insert 1000a. The tipping paper 2255 may be a high-permeability cigarette paper, or a perforated paper, as an example. The tipping paper 2255 may have a perforation density, and/or a perforation size, that may very axially to allow for a uniform air distribution and a greater utilization of the tobacco element. The tipping paper 2255 may provide an overall stiffness to the insert 1000a, or a portion of the insert 1000a. An aluminum foil 2265 may also be used to contain portions of the insert 1000a, and this aluminum foil 2265 may either be included in lieu of the tipping paper 2255, or in addition to the tipping paper 2255.

The insert 1000a may either be permanently affixed within the cartridge 70a, or alternatively the insert 1000a may be removable and replaceable within the cartridge 70a, where the insert 1000a may be accessed by removing the mouth-end insert 8 from the end of the cartridge 70a.

FIG. 3B illustrates another e-vaping cartridge 74a with a tobacco element 2250 in an insert 1002a, in accordance with an example embodiment. This cartridge 74a may be connected to a power section, such as the power section 72 of FIG. 2. Elements of this cartridge 74a which are common to the elements of cartridge 74 of FIG. 2, are not described herein, for brevity sake. The insert 1002a may share the same specifications and characteristics as the insert 1000a of FIG. 3A, with the exception of the differences described herein.

The insert 1002a of FIG. 3B may be located at an end of the cartridge 74a, where the inserts 1002a may therefore take the place of a mouth-end insert (such as the mouth-end insert 8 of FIG. 3A). A gap G2 may exist between an outer surface of the tobacco element 2250 and an inner diameter of the housing 6b of the cartridge 74a, where this gap G2 may exist along a longitudinal length of the tobacco element 2250 (although the gap G2 may not be a consistent depth along the longitudinal length of the tobacco element 2250). In an embodiment, the gap G2 may narrow to a non-existent depth (i.e., a negligible, or nonexistent depth), at the union between the tobacco element 2250 and the filter 2260), where the gap G2 may be larger, or largest, at the end of the tobacco element 2250 that faces the heater 14. The gap G2 may have the same characteristics as the gap G1 described above.

The filter 2260 may include an end with a recessed (depressed) area 2280, where the end of the tobacco element 2250 may be somewhat embedded within the filter 2260 at the union between the tobacco element 2250 and the filter 2260, in order to provide extra stability for the overall insert 1002a (it should be understood that insert 1000a FIG. 3A may also include this feature). Therefore, an adhesive 2270 may be used to connect the tobacco element 2250 with the filter 2260, where the adhesive 2270 may reside in one or more spot locations within the recessed area 2280 of the filter 2260, or alternatively the adhesive 2270 may effectively cover the union (within the recessed area 2280) between the tobacco element 2250 and the filter 2260. Alternatively to a recessed area 2280 within the filter 2260, the union between the tobacco element 2250 and the filter 2260 of insert 1002a may instead be a flat surface, such that the recessed area 2280 does not exist (thereby making the union between the tobacco element 2250 and the filter 2260 the same as the insert 1000a of FIG. 3A).

Similar to the insert 1000a of FIG. 3A, the insert 1002a of FIG. 3B may be positioned within the outer air passage 9a rather than the second outer air passage 9b (or, multiple inserts 1002a may be located in the cartridge 74a, where at least one insert 1002a may be in the outer passage 9a, and at least another insert 1002a may be positioned in the second outer air passage 9b).

FIG. 4A illustrates an e-vaping cartridge 70b with a tobacco element 3250 in a non-combustible tobacco vaping insert 1000b, in accordance with an example embodiment. This cartridge 70b may be connected to a power section, such as the power section 72 of FIG. 1. Elements of this cartridge 70b which are common to the elements of cartridge 70 of FIG. 1, are not described herein, for brevity sake. The specification and characteristics of the insert 1000b, including a location of insert 1000b within cartridge 70b, may be identical to the inserts 1000a and 1002a (described above). Therefore, only the unique characteristics of insert 1000b are described herein. In particular, a gap between the tobacco element 3250 and an inner surface of the passage that the tobacco insert 3250 resides in (such as the gap between the tobacco element 3250 and an inner surface of housing 6b), may vary greatly along the longitudinal length of the tobacco element 3250. Specifically, the tobacco element 3250 may be a cone and/or somewhat conical shape, where a side cross-sectional view of the tobacco element 3250 may have a somewhat triangular shape. In this embodiment, the leading distal-edge of the tobacco element 3250 (the leading edge facing heater 14) may have a relatively large gap G3, whereas the proximal-edge of the tobacco element 3250 (the edge contacting the filter 2260) may have a relatively small gap G4. In an embodiment, the gap G4 at the proximal-edge may approach zero, such that the gap G4 may be negligible or non-existent (similar to the insert 1002b shown in FIG. 4B).

In an embodiment, the tobacco element 3250 may have a major diameter of about 6-10 mm (at the widest portion of the element 3250), where the gap between the outer surface of element 3250 and the housing 6b may taper down to about 2-4 mm in thickness (as signified by the gap G4), if the insert 1000b resides within the second outer air passage 9b of the cartridge 70a. In an embodiment, the gap G3/G4 thickness may be in a range between about 5% and 40% of the linear length of the major diameter of the tobacco element 3250 (or, about 5% to 40% of the linear length of the major diameter of the filter 2260), where the thickness may be smallest at the end of the tobacco element 3250 that is closest to the discharge of the cartridge 70b (or, optionally the gap G3/G4 may taper down to a negligible, or non-existent gap, at the end of the tobacco element 3250 that is closest to the discharge of the cartridge 70b). The filter 2260 may have a major outer diameter that is about 6-10 mm, with a hole diameter (traversing through a length of the filter 2260) that may be about 2-4 mm.

Similar to the insert 1002a (shown in FIG. 3B, and described above), the filter 2260 may optionally have a recessed area that may add to the stability of the union between tobacco element 3250 and filter 2260.

FIG. 4B illustrates another e-vaping cartridge 74b with a tobacco element 3250 in an insert 1002b, in accordance with an example embodiment. This cartridge 74b may be connected to a power section, such as the power section 72 of FIG. 2. Elements of this cartridge 74b which are common to the elements of cartridge 74 of FIG. 2, are not described herein, for brevity sake. The specification and characteristics of the insert 1002b, including a location of insert 1002b within cartridge 74b, may be identical to the inserts 1000a and 1002a (described above). Therefore, only the unique characteristics of insert 1002b are described herein. As shown in FIG. 4B, the tobacco element 3250 may be a cone shape, such that a leading distal-end of the element 3250 may have a relatively large gap G5 within the housing 6b, where a size of the gap may decrease along a longitudinal length of the tobacco element 3250, such that a proximal-end of the tobacco element 3250 may reach a very small and/or negligible (non-existent) gap at the union between the tobacco element 3250 and the filter 2260. Alternatively, a small (non-negligible) gap at the proximal-end of the tobacco element 3250 may exist at the union between the tobacco element 3250 and the filter 2260, such that the tobacco element 3250 of insert 1002b may be configured to be the same as the tobacco element 3250 of the insert 1000b of FIG. 4A.

In an embodiment, the tobacco element 3250 may have a major diameter of about 6-10 mm (at the widest portion of the element 3250), where the gap G5 may taper down to about 2-4 mm in thickness, if the insert 1002b resides within the second outer air passage 9b of the cartridge 74b. In an embodiment, the gap G5 thickness may range be between about 5% and 40% of the linear length of the major diameter of the tobacco element 3250 (or, about 5% to 40% of the linear length of the major diameter of the filter 2260), where the thickness may be smallest at the end of the tobacco element 3250 that is closest to the discharge of the cartridge 74b (or, optionally the gap G5 may taper down to a negligible, or non-existent gap at the end of the tobacco element 3250 that is closest to the discharge of the cartridge 74b, as shown in FIG. 4B). The filter 2260 may have a major outer diameter that is about 6-10 mm, with a hole diameter (traversing through a length of the filter 2260) that may be about 2-4 mm.

FIG. 5A illustrates an e-vaping cartridge 70c with a tobacco element for 4250 in a non-combustible tobacco vaping insert 1000c, in accordance with an example embodiment. This cartridge 70c may be connected to a power section, such as the power section 72 of FIG. 1. Elements of this cartridge 70c which are common to the elements of cartridge 70 of FIG. 1, are not described herein, for brevity sake. The specification and characteristics of the insert 1000c, including a location of insert 1000c within cartridge 70c, may be identical to the inserts 1000a and 1002a (described above). Therefore, only the unique characteristics of insert 1000c are described herein. In particular, the insert 1000c may include a tobacco element 4250 that may be in the form of a relatively thin tobacco sheet. That is to say, the tobacco element 4250 may be a rectangular, cylindrical, triangular, or cone shape (or, any other shape) that may be hollow, or relatively hollow, on an inside of the tobacco element 4250. In an embodiment, the tobacco element 4250 may have a thickness that may be preferably about 2-4 mm (which may be dependent on the overall size of the cartridge).

A gap G6 may exist between the outer surface of the tobacco element for 250 and the vapor passage that the insert 1000c resides within (where the insert 1000c may reside in the second outer air passage 9b, or in the outer air passage 9a, or in an embodiment where at least one insert 1000c resides in both of these locations). The gap G6 may exist along the longitudinal length of tobacco element 4250, where this gap may or may not be uniform along the length of the element 4250. In an embodiment, the gap G6 may decrease and become negligible, or nearly negligible, near the proximal-end of the tobacco element 4250 (i.e., near the end of the tobacco element 4250 that contacts the filter 2260).

In an embodiment, the tobacco element 4250 may have a major diameter of about 6-10 mm (at the widest portion of the element 4250), where the gap G6 may taper down to about 2-4 mm in thickness, if the insert 1000c resides within the second outer air passage 9b of the cartridge 70c. In an embodiment, the gap G6 thickness may be between about 5% and 40% of the linear length of the major diameter of the tobacco element 4250 (or, about 5% to 40% of the linear length of the major diameter of the filter 2260), at the end of the tobacco element 4250 that is closest to the discharge of the cartridge 70c (or, optionally the gap G6 may taper down to a negligible, or non-existent gap at the end of the tobacco element 4250 that is closest to the discharge of the cartridge 70c). The filter 2260 may have a major outer diameter that is about 6-10 mm, with a hole diameter (traversing through a length of the filter 2260) that may be about 2-4 mm.

An adhesive 2270 may be used to connect the proximal-end of the tobacco element 4250 to the filter 2260, where the adhesive may be applied in either spot locations, or alternatively the adhesive 2270 may be applied to all contact surfaces between the tobacco element 4250 and the filter 2260. In an alternative embodiment, the filter 2260 may include recessed areas, identical to the recessed areas 2280 of the insert 1002c (shown in FIG. 5B), in order to increase the stability of the insert 1000c.

Figure 5B:
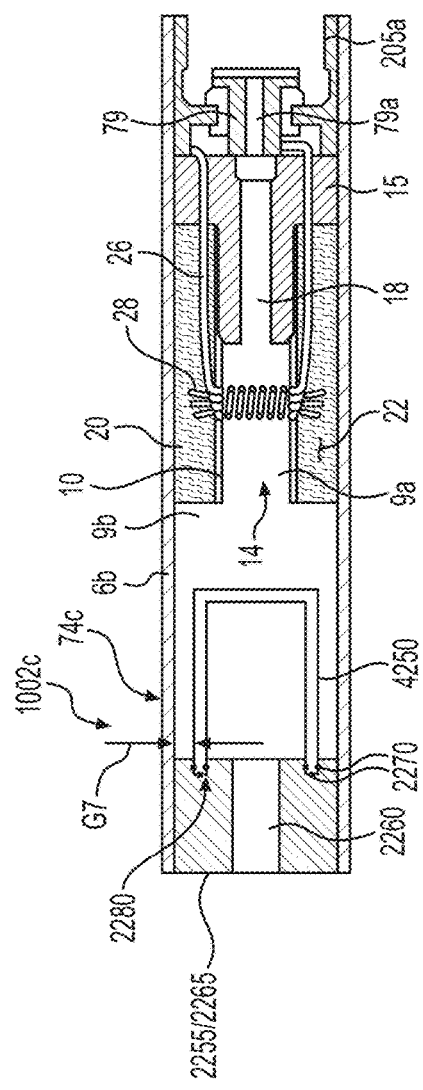
FIG. 5B illustrates another e-vaping cartridge with a non-combustible tobacco vaping insert including a tobacco element in the shape of a sheet, in accordance with an example embodiment.

FIG. 5B illustrates another e-vaping cartridge 74c with a tobacco element for 4250 in a non-combustible tobacco vaping insert 1002c, in accordance with an example embodiment. This cartridge 74c may be connected to a power section, such as the power section 72 of FIG. 2. Elements of this cartridge 74c which are common to the elements of cartridge 74 of FIG. 2, are not described herein, for brevity sake. The specification and characteristics of the insert 1002c, including a location of insert 1002c within cartridge 74c, may be identical to the inserts 1000a and 1002a (described above). Therefore, only the unique characteristics of insert 1002c are described herein. As shown in FIG. 5B, the insert 1002c may include a tobacco element 4250 that may be a thin sheet (identical to the thin sheet tobacco insert 4250 of insert 1000c, shown in FIG. 5A), where the filter 2260 may include a recessed area 2280 that is able to stably hold a proximal-end of the tobacco element 4250 to the filter, via an adhesive 2270.

Similar to the insert 1000c (of FIG. 5A), the gap G7 of insert 1002c may either be a uniform, or non-uniform gap, that may exist along the longitudinal length of the tobacco element 4250. In an embodiment, the gap G7 may decrease along the length of the tobacco element 4250, such that gap G7 may decrease to a negligible, or near-negligible gap, at the proximal-end of the tobacco element 4250 (i.e., the end of element 4250 that is contacting the filter 2260).

In an embodiment, the tobacco element 4250 may have a major diameter of about 6-10 mm (at the widest portion of the element 4250), where the gap G7 may taper down to about 2-4 mm in thickness, if the insert 1002c resides within the second outer air passage 9b of the cartridge 74c. In an embodiment, the gap G7 thickness may be between about 5% and 40% of the linear length of the major diameter of the tobacco element 4250 (or, about 5% to 40% of the linear length of the major diameter of the filter 2260), at the end of the tobacco element 4250 that is closest to the discharge of the cartridge 74c (or, optionally the gap G7 may taper down to a negligible, or non-existent gap at the end of the tobacco element 4250 that is closest to the discharge of the cartridge 74c). The filter 2260 may have a major outer diameter that is about 6-10 mm, with a hole diameter (traversing through a length of the filter 2260) that may be about 2-4 mm.

General Information for the Example Structural Embodiments

Based on the discussion of the structural components of the cartridges described in FIGS. 3A/B, 4A/B and 5A/B, it should be understood that a location of any of the inserts may be positioned at any location between the heater 14 and a proximal-end of the respective cartridges (whether or not the proximal-end of the cartridges have a mouth-end insert 8, or not). Each of the inserts may also either be permanently affixed within the respective cartridge, or alternatively removable and replaceable within the respective cartridge. Furthermore, each of the tobacco elements of the respective inserts may optionally be recessed within the filter (as depicted for instance in FIGS. 3B and 5B), in order to add to the overall stability of each of the inserts.

Furthermore with regard to the example structural embodiments described above, each of the cartridges (depicted in FIGS. 3A/B, 4A/B and 5A/B) may either be disposable, or rechargeable and reusable. In the event that the cartridges are rechargeable and reusable, either the inserts within the cartridges may be replaceable, or the pre-vapor formulation within the cartridges may be rechargeable, or both. In an alternative embodiment, each of the inserts cartridges may not include a filter 2260.

Performance of Example Embodiments

Figure 6:
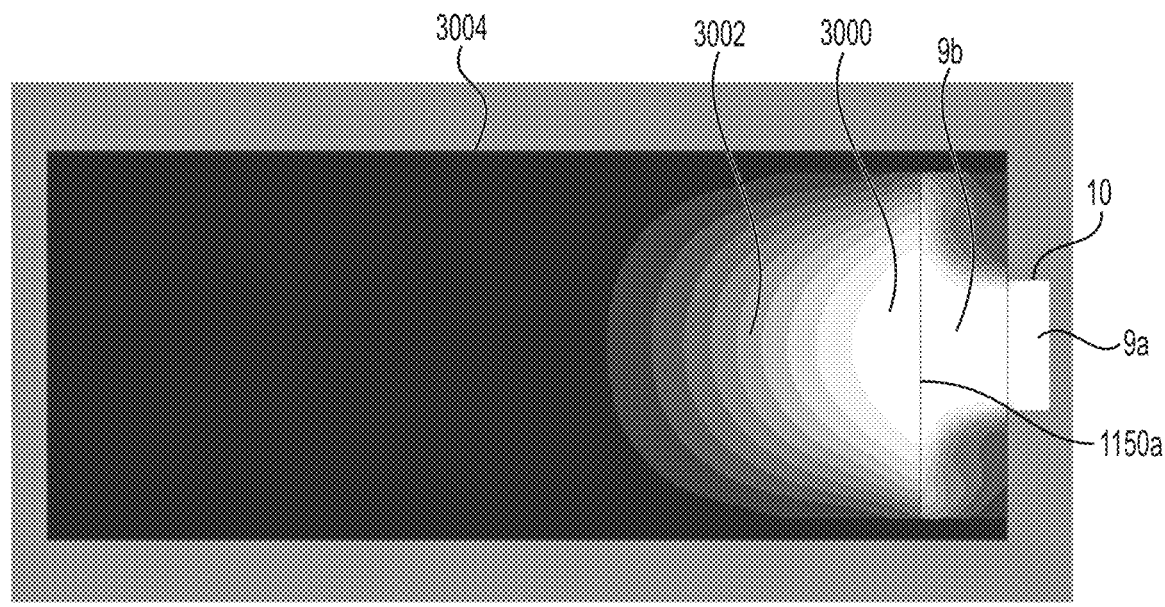
FIG. 6 illustrates a temperature profile of the e-vaping device shown in FIG. 1.

FIG. 6 illustrates a temperature profile of an e-vaping device that may be similar to the device 60 shown in the configuration of FIG. 1. As shown in the profile, heated vapor flows through the outer air passage 9a at a relatively high heat (approximately 200° C.), and enters the second outer air passage 9b, where the vapor then contacts a leading surface 1150a of the tobacco element 1150. As the heated vapor flows through the tobacco element 1150, the vapor rapidly transitions from a high-heat region 3000 of tobacco element 1150 (as shown by the white region of FIG. 6), to a medium-heat area 3002 of the tobacco element 1150, and then to a low-heat area 3004 of the element 1150. In other words, in a configuration such as FIG. 1 where the housing 1185 and tobacco element 1150 of a non-combustible tobacco vaping insert 1000 fully occupies the inner diameter of the vapor flow path (in the case, the insert 1000 fully occupies the inner diameter of the second outer air passage 9b), the heated vapor that flows through the insert 1000 is quickly cooled (to near ambient temperatures), prior to the heated vapor being able to travel fully through the entire length of the insert 1000. This heating profile, in conjunction with the associated significant pressure drop of the vapor passing through the insert 1000, may be undesirable due to the configuration of the insert 1000.

Figure 7:
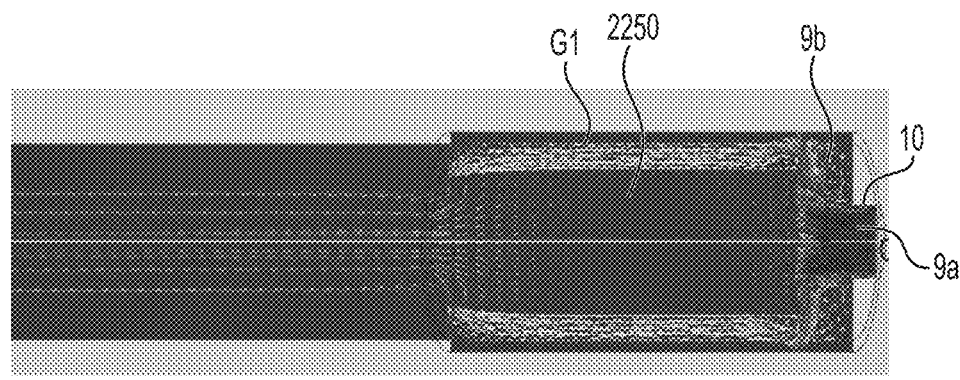
FIG. 7 illustrates a velocity profile of an e-vaping device with the cartridge of FIG. 3A, in accordance with an example embodiment.

FIG. 7 illustrates a velocity profile of an e-vaping device with a cartridge similar to the cartridge 70c of FIG. 3A, in accordance with an example embodiment. As depicted in this figure, relatively higher velocity vapor (depicted as high-density white lines, in FIG. 7) is seen directly above and below the location of the tobacco element 2250 (i.e., within the gap G1), which in turn causes an even distribution of vapor to permeate through all outer surfaces of the tobacco element 2250. This indicates a greater mixture of the vapor with the tobacco element 2250 of the insert 1000a (where similar performance data was also experienced for the other tobacco elements of the other inserts that are described above). Similar velocity profile test results were also found for the inserts shown in the example embodiments that are included in FIGS. 3B, 4A, 4B, 5A and 5B.

Figure 8:
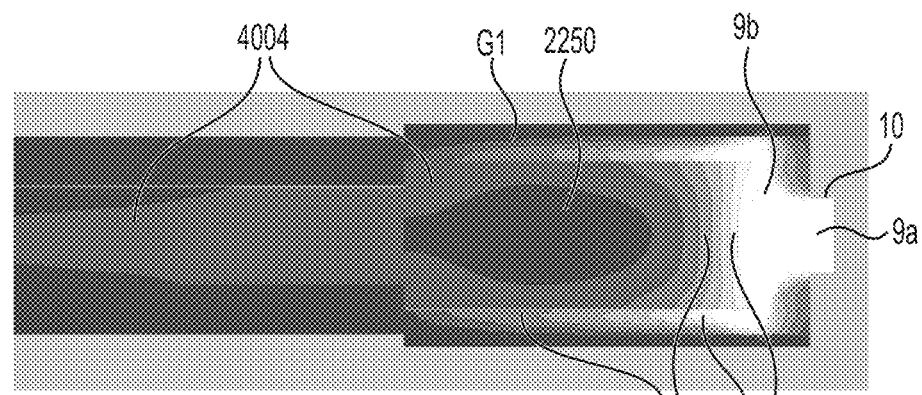
FIG. 8 illustrates a temperature profile of an e-vaping device with the cartridge of FIG. 3A, in accordance with an example embodiment.

FIG. 8 illustrates a temperature profile of an e-vaping device with a cartridge similar to the cartridge 70c of FIG. 3A, in accordance with an example embodiment. As depicted in this figure, the temperature profile is in sharp contrast to the profile shown in FIG. 6 (described above). Specifically, the high-heat area 4000 emanates around a significantly greater surface area of the tobacco element 2250 (as compared to FIG. 6), where the medium-heat area 4002 fully penetrates a greater volumetric portion of the tobacco element 2250, and the low-heat area 4004 not only fully penetrates the tobacco element 2250 but also extends to the discharge end of the cartridge 70a. This indicates a much greater mixing of relatively higher-heat vapor with the tobacco element 2250, as the shape in geometry of the tobacco element 2250 allows the heated vapor to permeate throughout the tobacco element 2250 of the insert 1000a. Similar temperature profile test results were also found for the inserts shown in the example embodiments that are included in FIGS. 3B, 4A, 4B, 5A and 5B. The temperature profile of FIG. 8, in conjunction with the velocity profile shown in FIG. 7, indicates that the improved shape and geometric configuration of the tobacco elements 2250 in insert 1000a (and likewise, in the inserts 1002a, 1000b, 1002b, 1000c and 1002c, described above) provide a more uniform tobacco heating with a shorter average vapor flow path through the insert 1000a, thereby resulting in less vapor loss, lower pressure drop, higher exit temperatures and a greater level of flavoring of the vapor.

Example embodiments having thus been described, it will be obvious that the same may be varied in many ways. Such variations are not to be regarded as a departure from the intended spirit and scope of example embodiments, and all such modifications as would be obvious to one skilled in the art are intended to be included within the scope of the following claims.

What is claimed is:

1. A tobacco vaping insert, comprising:
   a filter having a first diameter; and
   a tobacco element with a first end contacting the filter, at least one first portion of the tobacco element having a second diameter that is smaller than the first diameter of the filter,
   the tobacco element having a varying diameter, the first end of the tobacco element having a third diameter,
   the third diameter being a largest diameter of the tobacco element, along a longitudinal length of the tobacco element.

2. The tobacco vaping insert of claim 1, wherein the third diameter of the tobacco element is smaller than the first diameter of the filter.

3. The tobacco vaping insert of claim 1, wherein the third diameter of the tobacco element is equal to the first diameter of the filter.

4. The tobacco vaping insert of claim 1, wherein the tobacco element is a conical shape.

5. The tobacco vaping insert of claim 1, wherein the first end of the tobacco element is connected to the filter via an adhesive, the adhesive being at least one of a starch-based adhesive and a dextrin-based adhesive.

6. The tobacco vaping insert of claim 1, wherein the tobacco element includes at least one of tobacco leaf, compressed tobacco, tobacco strands, rolled tobacco, reconstituted tobacco, filler, tobacco beads, compressed tobacco rod, shaped tobacco and tobacco powder.

7. The tobacco vaping insert of claim 6, wherein the tobacco element further includes flavoring elements, the flavoring elements being one of a tobacco-flavoring and another flavoring that is not tobacco-flavoring.

8. The tobacco vaping insert of claim 1, wherein the filter is one of a cellulose acetate (CA) filter and a hollow-acetate-tube (HAT) filter.

9. A tobacco vaping insert, comprising:
   a filter having a first diameter; and
   a tobacco element with a first end contacting the filter, wherein at least one first portion of the tobacco element has a second diameter that is smaller than the first diameter of the filter wherein the first end of the tobacco element is embedded into a surface of the filter.

10. The tobacco vaping insert of claim 9, wherein the first end of the tobacco element is connected to the filter via an adhesive, the adhesive being at least one of a starch-based adhesive and a dextrin-based adhesive.

11. A cartridge including a tobacco vaping insert, comprising:
a housing;
a reservoir within the housing, the reservoir configured to contain a pre-vapor formulation;
a first tube extending longitudinally within the housing, wherein at least one of the first tube and the housing at least partially defines an air passage;
a wick in communication with at least one first portion of the air passage, distal ends of the wick being in communication with the reservoir;
a heater configured to vaporize the pre-vapor formulation that is communicated to the heater by the wick; and
a tobacco vaping insert being positioned in at least one second portion of the air passage, the tobacco vaping insert being configured to allow vapor that is generated by the heater to pass through the tobacco vaping insert prior to being discharged from the cartridge, the tobacco vaping insert including,
a filter having a first diameter, and
a tobacco element with a first end contacting the filter, at least one first portion of the tobacco element having a second diameter that is smaller than the first diameter of the filter.

12. The cartridge of claim 11, wherein the first diameter of the filter of the tobacco vaping insert fills a diameter of the at least one second portion of the air passage, and an annular gap exists between at least a portion of an outer surface of the tobacco element of the tobacco vaping insert and the at least one second portion of the air passage, along at least a portion of a longitudinal length of the tobacco element.

13. The cartridge of claim 12, wherein the annular gap exists along a longitudinal length of the tobacco element.

14. The cartridge of claim 12, wherein the annular gap varies in thickness along a longitudinal length of the tobacco element.

15. The cartridge of claim 12, wherein the annular gap has a thickness that is about 5% to 40% of a linear length of the first diameter of the filter.

16. The cartridge of claim 11, wherein the heater is configured to be in thermal communication with the tobacco element in order to heat at least a portion of the tobacco element.

17. A tobacco vaping insert, comprising:
a filter having a first cross-sectional width; and
a tobacco element with a first end contacting the filter, at least one first portion of the tobacco element having a second cross-sectional width that is smaller than the first cross-sectional width of the filter,
the tobacco element having a varying cross-sectional width, the first end of the tobacco element having a third cross-sectional width,
the third cross-sectional width being a largest cross-sectional width of the tobacco element, along a longitudinal length of the tobacco element.

* * * * *